United States Patent [19]

Carrico

[11] Patent Number: 5,200,313
[45] Date of Patent: * Apr. 6, 1993

[54] NUCLEIC ACID HYBRIDIZATION ASSAY EMPLOYING DETECTABLE ANTI-HYBRID ANTIBODIES

[75] Inventor: Robert J. Carrico, Elkhart, Ind.

[73] Assignee: Miles Inc., Elkhart, Ind.

[*] Notice: The portion of the term of this patent subsequent to May 10, 2005 has been disclaimed.

[21] Appl. No.: 188,114

[22] Filed: Apr. 25, 1988

Related U.S. Application Data

[63] Continuation of Ser. No. 707,420, Mar. 1, 1985, abandoned, which is a continuation-in-part of Ser. No. 616,132, Jun. 1, 1984, abandoned, and a continuation-in-part of Ser. No. 626,927, Jul. 9, 1984, abandoned, which is a continuation-in-part of Ser. No. 520,524, Aug. 5, 1983, abandoned.

[51] Int. Cl.$^5$ ............................................. C12Q 1/68
[52] U.S. Cl. ..................................... 435/6; 435/7.1; 435/803; 435/810; 436/501; 436/508; 436/512; 436/808; 536/24.32; 530/387.1; 935/2; 935/78
[58] Field of Search ............... 435/6, 7, 803, 810; 935/2, 78; 536/27; 530/387; 436/501, 508, 512, 808

[56] References Cited

U.S. PATENT DOCUMENTS

| | | | |
|---|---|---|---|
| 4,298,685 | 11/1981 | Parikh et al. | 436/530 X |
| 4,358,535 | 11/1982 | Falkow et al. | |
| 4,563,417 | 1/1986 | Albarella et al. | 935/77 X |
| 4,581,333 | 4/1986 | Kourilsky | |
| 4,623,627 | 11/1986 | Huang et al. | 835/78 X |
| 4,626,501 | 12/1986 | Landes | 935/77 X |
| 4,732,847 | 3/1988 | Stuart et al. | |
| 4,743,535 | 5/1988 | Carrico | 935/78 X |

FOREIGN PATENT DOCUMENTS 0135159  3/1985  European Pat. Off.
2019408 10/1979  United Kingdom.

OTHER PUBLICATIONS

Bolden, A. et al *J. Virology*, vol. 16, No. 6, 1975, pp. 1584–1592.
Martinell, J. et al *Proc. Natl. Acad. Sci. USA*, vol. 78, 1981 pp. 5056–5060.
Schwartz, E. F. et al., Chem. Abst. 70(25):113344d(1969), p. 168.
Stumph, W. E. et al., Biochemistry 17(36):5791–5798(1978).
Raap, A. K. et al., Histochemistry 81:517–520(1984).
Poirier, M. C. et al., Proc. Natl. Acad. Sci. USA 79:6443–6447 (1982).
Stuart, W. D. et al., Proc. Natl. Acad. Sci. USA 78:3751–3754(1981).
Reddy, A. R. et al., Biochem. Biophys. Res. Commun. 103:959–967(1981).
Rudkin, G. T. et al., Nature 265:472–473(1977).
Van Prooijen-Knedt, A. C. et al., Exp. Cell Res. 141:397–407(1982).

*Primary Examiner*—Amelia Burgess Yarbrough
*Assistant Examiner*—Ardin H. Marschel
*Attorney, Agent, or Firm*—Andrew L. Klawitter

[57] ABSTRACT

A nucleic acid hybridization assay employing an immobilized or immobilizable polynucleotide probe selected to form DNA.RNA or RNA.RNA hybrids with the particular polynucleotide sequence to be determined. Resulting hybrids are detected by binding of an antibody reagent, preferably labeled with a detectable chemical group, selective for binding the hybrids in the presence of the single stranded sample and probe nucleic acids. No immobilization or labeling of sample nucleic acids is necessary and hybridization can be performed entirely in solution.

9 Claims, 2 Drawing Sheets

NUCLEIC ACID HYBRIDIZATION ASSAY EMPLOYING DETECTABLE ANTI-HYBRID ANTIBODIES

CROSS-REFERENCE TO RELATED APPLICATION

This is a continuation of application Ser. No. 707,420, filed Mar. 1, 1985, now abandoned, which is both a continuation-in-part of application Ser. No. 616,132, filed Jun. 1, 1984, now abandoned, and a continuation-in-part of application Ser. No. 626,927, filed Jul. 9, 1984 is now abandoned, which is a continuation-in-part of application Ser. No. 520,524, filed Aug. 5, 1983, now abandoned.

FIELD OF THE INVENTION

This invention relates to nucleic acid hybridization assay methods and reagent systems for detecting specific polynucleotide sequences. The principle of nucleic acid hybridization assays was developed by workers in the recombinant DNA field as a means for determining and isolating particular polynucleotide base sequences of interest. It was found that single stranded nucleic acids, e.g., DNA and RNA, such as obtained by denaturing their double stranded forms, will hybridize or recombine under appropriate conditions with complementary single stranded nucleic acids. By labeling such complementary probe nucleic acids with some readily detectable chemical group, it was then made possible to detect the presence of any polynucleotide sequence of interest in a test medium containing sample nucleic acids in single stranded form.

In addition to the recombinant DNA field, the analytical hybridization technique can be applied to the detection of polynucleotides of importance in the fields of human and veterinary medicine, agriculture, and food science, among others. In particular, the technique can be used to detect and identify etiological agents such as bacteria and viruses, to screen bacteria for antibiotic resistance, to aid in the diagnosis of genetic disorders such as sickle cell anemia and thalassemia, and to detect cancerous cells. A general review of the technique and its present and future significance is provided in Biotechnology (August 1983), pp. 471-478.

BACKGROUND INFORMATION

The following information is provided for the purpose of making known information believed by the applicant to be of possible relevance to the present invention. No admission is necessarily intended, nor should be construed, that any of the following information constitutes prior art against the present invention.

The state-of-the-art nucleic acid hybridization assay techniques generally involve immobilization of the sample nucleic acid on a solid support. Hybridization between particular base sequences or genes of interest in the sample nucleic acid is determined by separating the solid support from the remainder of the reaction mixture which contains unbound labeled probe, followed by detection of the label on the solid support.

The need to immobilize sample nucleic acids in order to conduct the state-of-the-art hybridization assay poses two significant problems. Firstly, the procedures required to accomplish immobilization are generally time consuming and add a step which is undesirable for routine use of the technique in a clinical laboratory. Secondly, proteins and other materials in the heterogeneous sample, particularly in the case of clinical samples, can interfere with the immobilization of the nucleic acids.

As alternatives to immobilizing sample nucleic acids and adding labeled probe, one can use an immobilized probe and label the sample nucleic acids in situ, or one can use a dual hybridization technique requiring two probes, one of which is immobilized and the other labeled [Methods in Enzymology 65:468(1968) and Gene 21:77-86(1983)]. The former alternative, however, is even less desirable since the in situ labeling of the sample nucleic acids requires a high degree of technical skill which is not routinely found in clinical technicians and there are no simple, reliable methods for monitoring the labeling yield, which can be a significant problem if the labeling media contain variable amounts of inhibitors of the labeling reaction. The dual hybridization technique has the disadvantages of requiring an additional reagent and incubation step and the kinetics of the hybridization reaction can be slow and inefficient. The accuracy of the assay can also be variable if the complementarity of the two probes with the sample sequence is variable.

Techniques for directly detecting the polynucleotide duplex formed as the product of hybridization between the sample and probe polynucleotides, and thereby dispensing with the chemical labeling and immobilization of sample or probe polynucleotides, have been generally unsatisfactory. Attempts to generate antibodies which will selectively bind double stranded DNA.DNA hybrids over single stranded DNA have failed [Parker and Halloran, "Nucleic Acids in Immunology", ed. Plescia and Braun, Springer-Verlag, N.Y. (1969) pp. 18 et seq]. Some success has been achieved in generating antibodies that will bind DNA.RNA mixed hybrids or RNA.RNA hybrids and have low affinity for the single stranded polynucleotides [see, for example, Rudkin and Stollar, Nature 265:472(1977)]. Rudkin and Stollar fixed whole cells on microscope slides and exposed the DNA in the nucleus. It was hybridized with an RNA probe and the hybrid was detected by fluorescence microscopy with fluorescein-labeled antibody to DNA.RNA. However, these methods are described, as in the case of the hybridization techniques discussed above employing labeled probes, as requiring immobilization of the sample nucleic acids. Immobilization of cellular DNA for in situ hybridization is particularly tenuous because the DNA must remain fixed to delicate cell residues during the hybridization and immunochemical detection steps. The results observed by fluorescence microscopy do not give quantitative data on the amount of hybrid formed.

Accordingly, there is an established need for a nucleic acid hybridization assay which does not require the immobilization or labeling of sample nucleic acids, and which does not require dual probes. Further, such technique should allow the use of a variety of labels, particularly of the nonradioisotopic type. A nucleic acid hybridization assay method and reagent system having these and other advantages are principal objectives of the present invention.

SUMMARY OF THE INVENTION

A nucleic acid hybridization assay method has now been devised which eliminates the need to immobilize or label sample nucleic acids and which requires but a single probe element. The present invention provides a method for determining a particular polynucleotide sequence in an appropriate test medium containing single stranded nucleic acids. The test medium is combined with an immobilized or immobilizable polynucleotide probe, comprising at least one single stranded base sequence which is substantially complementary to the sequence to be determined, under conditions favorable to hybridization between the sequence to be determined and the complementary probe sequence. The complementary probe sequence will be selected to be substantially composed of RNA when the sequence to be determined is RNA or DNA, that is, such probe sequence can be selected to be RNA whether the sample sequence of interest is RNA or DNA. Alternatively, when the sample sequence of interest is RNA, the complementary probe sequence can be selected to be substantially composed of either DNA or RNA. Thus, hybrids resulting from hybridization between the probe and the sample sequence will be DNA.RNA or RNA.RNA duplexes.

The resulting hybrids can then be detected, after or simultaneously with immobilization of the probe where such was combined with the test medium in an immobilizable form, by addition of an antibody reagent capable of binding to the DNA.RNA or RNA.RNA duplexes formed and determining the antibody reagent that becomes bound to such duplexes. A variety of protocols and reagent combinations can be employed in order to carry out the principles of the present method. Important features of the present invention are that the sample nucleic acids are not immobilized or required to be labeled before contact with the probe.

The antibody reagent is the key to specific and sensitive detection of hybridization between the probe and sample nucleic acids. Of course, whole antibodies or appropriate fragments and polyfunctional forms thereof can be used as described more fully below, and it will be understood that, when used in this disclosure and the claims which follow, the term antibody reagent will mean whole antibodies and their polyfunctional and fragmented forms as well, unless otherwise noted.

Determination of binding of the antibody reagent to hybridization duplexes can be accomplished in any convenient manner. It is preferred that the antibody reagent be labeled with a detectable chemical group such as an enzymatically active group, a fluorescer, a chromophore, a luminescer, a specifically bindable ligand, or a radioisotope, the nonradioisotopic labels being especially preferred. The labeled antibody reagent which becomes bound to resulting immobilized hybrid duplexes can be readily separated from that which does not become so bound and the detectable chemical group or label is measured in either separated fraction, usually the former.

By eliminating the need to immobilize or label the sample nucleic acids, the present invention provides a highly advantageous hybridization assay technique. The analyst is not required to have the high level of skill or to take the requisite time to perform the immobilization or labeling procedures. Moreover, there is complete elimination of the potential for sample interferences with the immobilization procedure. The test kit provided to the clinical user would include the probe already immobilized or in a readily immobilizable form such as by binding to an immobilized binding partner. In the prior art systems, interferences from extraneous proteins and other materials in the sample can be a serious problem whether the sample nucleic acids to be immobilized are RNA or DNA.

In the prior art methods, immobilization is accomplished by adsorption onto a microporous membrane, such as nitrocellulose, or by covalent bonding to reactive sites on a solid support. In the first case, proteins from the sample can coat the surface and block the adsorption of nucleic acids. Furthermore, many procedures require baking at elevated temperatures, commonly higher than 80° C., in vacuo to fix adsorbed nucleic acids to the support. If mucus or other materials endogenous to the sample are present, they can become dried to the support to form a film that can adsorb the labeled probe during hybridization and increase the background signal and consequently decrease sensitivity. Also, if an enzyme or other protein is involved in the detection of the label, it can often bind nonspecifically to the film and contribute even further to the background problem. If covalent immobilization is employed, proteins and other materials from the sample can be expected to have available reactive groups which will engage in the coupling reaction and neutralize the coupling of the desired nucleic acids.

Since the present invention provides the probe in preferred embodiments in an already immobilized form or in a form which is readily immobilized by binding to an immobilized binding partner, the inefficiencies inherent in the prior art immobilization procedures are overcome and thus the detection limits of the assay are maintained. A further advantage is that nonspecific binding of sample RNA or DNA to the solid support will not be recognized by the antibody reagent. Therefore, the background signal will be low and the detection limit accordingly improved. Relative to the dual hybridization method which uses both a labeled probe and an immobilized probe, the labeled nucleotide can bind nonspecifically to the solid support and contribute background signal. This is not a possibility in the present method since no labeled probe is involved.

BRIEF DESCRIPTION OF THE DRAWINGS

The drawings are schematic representations of preferred methods for performing the present invention. The use of nucleic acid hybridization as an analytical tool is based fundamentally on the double stranded, duplex structure of DNA. The hydrogen bonds between the purine and pyrimidine bases of the respective strands in double stranded DNA can be reversibly broken. The two complementary single strands of DNA resulting from this melting or denaturation of DNA will associate (also referred to as reannealing or hybridization) to reform the duplexed structure. As is now well known in the art, contact of a first single stranded nucleic acid, either DNA or RNA, which comprises a base sequence sufficiently complementary to a second single stranded nucleic acid under appropriate solution conditions, will result in the formation of DNA.DNA, DNA.RNA, or RNA.RNA hybrids, as the case may be.

In the embodiment depicted in FIG. 1 of the drawings, the single stranded sample nucleic acids are brought into contact with the immobilized probe under favorable hybridization conditions. The resulting immobilized, hybridized duplexes, optionally after separating such duplexes from the remainder of the reaction mixture, are contacted with a labeled form of antibodies specific for the DNA.RNA or RNA.RNA duplexes. After washing to remove unbound labeled antibody, the label present on the solid support is measured.

Figure 1:
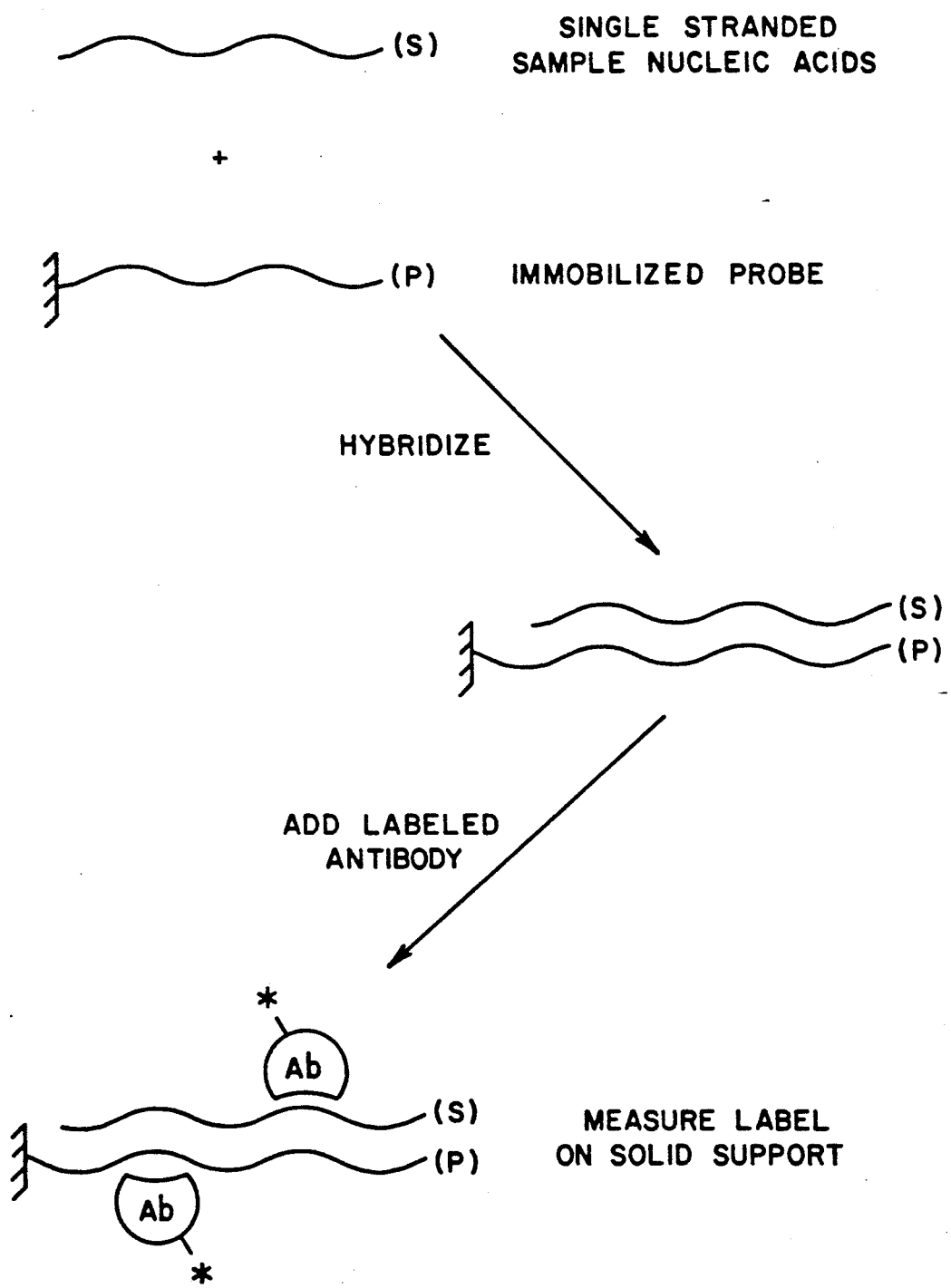
Figure 2:
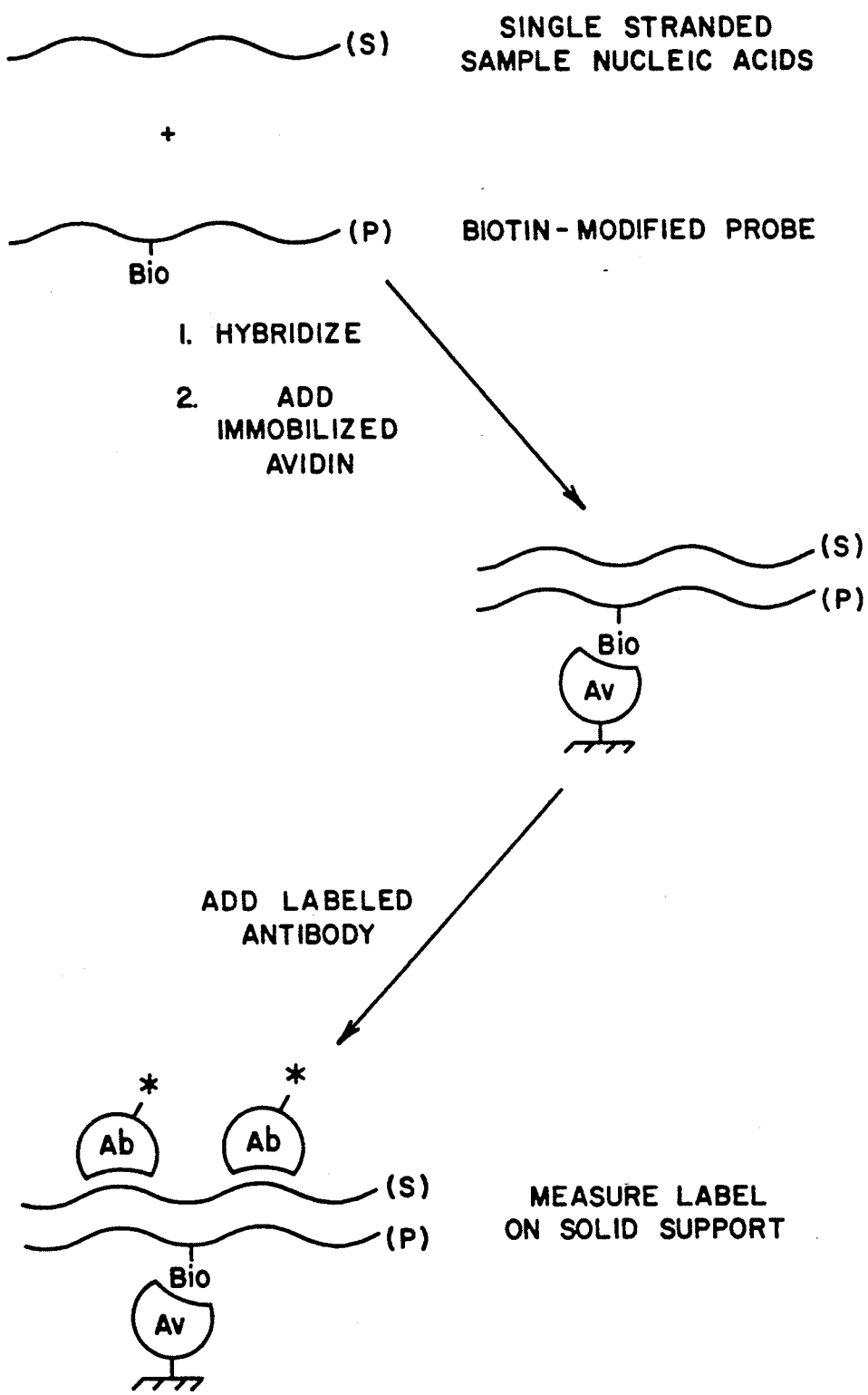

In the embodiment depicted in FIG. 2 of the drawings, the single stranded sample nucleic acids are contacted with a soluble form of the probe which has been appropriately chemically modified to comprise bindable biotin moieties. To the resulting soluble hybrids that are formed is added an immobilized form of avidin, a binding partner for biotin, resulting in formation of immobilized hybrids. The thus immobilized duplexes, optionally after separating them from the remainder of the reaction mixture, are contacted with labeled anti-hybrid antibodies, and after washing, the label present on the solid support is measured as above.

DESCRIPTION OF THE PREFERRED EMBODIMENTS

The Probe

The probe will comprise at least one single stranded base sequence substantially complementary to the sequence to be detected. However, such base sequence need not be a single continuous polynucleotide segment, but can be comprised of two or more individual segments interrupted by noncomplementary sequences. These nonhybridizable sequences can be linear, or they can be self-complementary and form hairpin loops. In addition, the complementary region of the probe can be flanked at the 3'- and 5'-termini by nonhybridizable sequences, such as those comprising the DNA or RNA of a vector into which the complementary sequence had been inserted for propagation. In either instance, the probe as presented as an analytical reagent will exhibit detectable hybridization at one or more points with sample nucleic acids of interest. Linear or circular single stranded polynucleotides can be used as the probe element, with major or minor portions being duplexed with a complementary polynucleotide strand or strands, provided that the critical homologous segment or segments are in single stranded form and available for hybridization with sample DNA or RNA, and provided that the antibody reagent selected for use with the probe does not significantly crossreact with the double stranded regions in the probe (e.g., where the antibody reagent is specific for DNA.RNA hybrids and the probe comprises RNA.RNA double stranded regions, or vice versa). The complementary probe sequence can be of any convenient or desired length, ranging from as few as a dozen to as many as 10,000 bases, and including oligonucleotides having less than about 50 bases.

The RNA or DNA probe can be obtained in a variety of conventional manners. For example, in the case of RNA probes, RNA can be isolated as the natural products of cells, such as 5s, 16s and 23s ribosomal RNAs from bacteria or cellular transfer RNAs. It is also practical to isolate specific messenger RNAs from cells which specialize in production of large amounts of a protein for which the messenger codes.

In vitro synthesis of RNA probes can be accomplished with a vector which contains the very active Salmonella typhimurium bacteriophage SP6 transcription promoter [Green et al (1983) Cell 32:681]. A vector with multiple restriction endonuclease sites adjacent to the promoter is available from Promega Biotec, Madison, Wis. A DNA probe is cloned into the vector which is then propagated in a bacterial host. Multiple RNA copies of the cloned DNA probe can be synthesized in vitro using DNA dependent RNA polymerase from bacteriophage SP6.

DNA probes can be prepared from a variety of sources. An entire bacterial genome can be immobilized for a hybridization assay designed to detect bacteria in a typically sterile sample. The assay would be capable of detecting abundant bacterial RNAs such as ribosimal RNAs and transfer RNAs. Alternatively, specific DNA sequences complementary to cellular RNAs can be cloned into well known plasmid or viral vectors and used as hybridization probes.

It should be understood that in using the expressions "RNA probe" and "DNA probe" herein, it is not implied that all nucleotides comprised in the probe be ribonucleotides or 2'-deoxyribonucleotides. The fundamental feature of an RNA or DNA probe for purposes of the present invention is that it be of such character to enable the stimulation of antibodies to DNA.RNA or RNA.RNA hybrids comprising an RNA or DNA probe which do not crossreact to an analytically significant degree with the individual single strands forming such hybrids. Therefore, one or more of the 2'-positions on the nucleotides comprised in the probe can be chemically modified provided the antibody binding characteristics necessary for performance of the present assay are maintained to a substantial degree. Likewise, in addition or alternatively to such limited 2'-deoxy modification, a probe can have in general any other modification along its ribose phosphate backbone provided there is no substantial interference with the specificity of the antibody to the double stranded hybridization product compared to its individual single strands.

Where such modifications exist in an RNA or DNA probe, the immunogen used to raise the antibody reagent would preferably comprise one strand having substantially corresponding modifications and the other strand being substantially unmodified RNA or DNA, depending on whether sample RNA or DNA was intended to be detected. Preferably, the modified strand in the immunogen would be identical to the modified strand in an RNA or DNA probe. An example of an immunogen is the hybrid poly(2'-0-methyladenylic acid).poly(2'-deoxythymidylic acid). Another would be poly(2'-O-ethylinosinic acid).poly(ribocytidylic acid). The following are further examples of modified nucleotides which could be comprised in a modified probe: 2'-O-methylribonucleotide, 2'-O-ethylribonucleotide, 2'-azidodeoxyribonucleotide, 2'-chlorodeoxyribonucleotide, 2'-O-acetylribonucleotide, and the phosphorothiolates or methylphosphonates of ribonucleotides or deoxyribonucleotides. Modified nucleotides can appear in probes as a result of introduction during enzymic synthesis of the probe from a template. For example, adenosine 5'-O-(1-thiotriphosphate) (ATPαS) and dATPαS are substrates for DNA dependent RNA polymerases and DNA polymerases, respectively. Alternatively, the chemical modification can be introduced after the probe has been prepared. For example, an RNA probe can be 2'-O-acetylated with acetic anhydride under mild conditions in an aqueous solvent [Steward, D. L. et al, (1972) Biochim. Biophys. Acta 262:227].

The critical property of an RNA or DNA probe for use herein is that antibodies raised against the probe duplexed with a complementary RNA or DNA strand, as desired, will discriminate in their binding properties between the duplexed form of the probe and single stranded nucleic acids. It is this property which enables detection of hybridized probe in the assay mixture without significant background binding to the unhybridized single stranded form of the probe or any nonspecifically bound single stranded sample nucleic acids. While as described above certain modifications along the ribonucleotide or deoxyribonucleotide strand can be tolerated without loss of antibody discrimination of the duplex from single strands, it will generally be preferable to employ RNA probes which are composed entirely of ribonucleotides when the sample polynucleotide is RNA or DNA. DNA probes can be used advantageously when the sample is RNA.

Immobilization of the Probe

As described previously, the probe will be presented for hybridization with sample nucleic acids in either an immobilized or an immobilizable form. An immobilizable form of the probe will be one in which the probe can be conveniently rendered immobilized subsequent to the hybridization reaction. The means by which the probe is ultimately immobilized is not critical to the present invention and any available approach can be taken so long as hybrids formed between the probe and the sequence of interest are rendered immobilized through a property of the probe. Thus, sample nucleic acids are not subjected to direct immobilization.

When presented to the hybridization reaction in an immobilized form, the probe can be in any appropriate form that enables the probe, and any components of the reaction mixture that have become associated therewith by hybridization and/or by binding of the anti-hybrid reagent, to be subsequently isolated or separated from the remaining mixture such as by centrifugation, filtration, chromatography, or decanting. A variety of compositions and configurations of an immobilized probe will thus be evident and available to the worker in the field. Essentially any form of the probe that is insoluble in the reaction mixture can be used. For example, the probe can be aggregated or otherwise precipitated, attached to an insoluble material, polymer, or support, or entrapped in a gel such as agarose or polyacrylamide [see Meth. Enzymol. 12B:635(1968) and PNAS 67:807(1970)]. It is particularly preferred to employ a solid support to which the probe is attached or fixed by covalent or noncovalent bonds, the latter including adsorption methods that provide for a suitably stable and strong attachment. The solid support can take on a variety of shapes and compositions, including microparticles, beads, porous and impermeable strips and membranes, the interior surface of reaction vessels such as test tubes and microtiter plates, and the like. Means for attaching a desired reaction partner to a selected solid support will be a matter of routine skill to the worker in the field.

One method for adsorbing the probe onto nitrocellulose membranes involves saturating a solution of probe with sodium iodide and spotting or filtering aliquots onto the membrane [Bresser et al (1983) DNA 2:243]. The sodium iodide facilitates denaturation of the probe and enhances adsorption onto the membrane. Alternatively, the probe can be treated with glyoxal, usually at concentrations around 1 molar(M), and then adsorbed onto the membrane. The probe is fixed by baking at around 80° C. under vacuum for a period in the range of 2-4 hours. [Thomas, P. S., (1983) Meth. in Enzymol. 100:255].

Covalent immobilization of RNA or DNA probes can also be accomplished. A wide variety of support materials and coupling techniques can be employed. For example, the probe can be coupled to phosphocellulose through phosphate groups activated by carbodiimide or carbonyldiimidazole [Bautz, E. K. F., and Hall, B. D., (1962) Proc. Nat'l. Acad. Sci. USA 48:400-408; Shih, T. Y., and Martin, M. A., (1974) Biochem. 13:3411-3418]. Also, diazo groups on m-diazobenzoyloxymethyl cellulose can react with guanine and thymidine residues of the polynucleotide [Noyes, B. E., and Stark, G. R., 5:301-310; Reiser, J., et al, (1978) Biochem. Biophys. Res. Commun. 85:1104-1112]. Polysaccharide supports can also be used with coupling through phosphodiester links formed between the terminal phosphate of the polynucleotide and the support hydroxyls by water soluble carbodiimide activation [Richwood, D., (1972) Biochim. Biophys. Acta 269:47-50; Gilham, P. T., (1968) Biochem. 7:2809-2813], or by coupling nucleophilic sites on the polynucleotide with a cyanogen bromide activated support [Arndt-Jovin, D. J., et al, (1975) Eur. J. Biochem. 54:411-418; Linberg, U., and Eriksson, S., (1971) Eur. J. Biochem. 18:474-479]. Further, the 3'-hydroxyl terminus of the probe can be oxidized by periodate and coupled by Schiff base formation with supports bearing amine or hydrazide groups [Gilham, P. T., (1971) Method. Enzymol. 21:191-197; Hansske, H. D., et al, (1979) Method. Enzymol. 59:172-181]. Supports having nucleophilic sites can be reacted with cyanuric chloride and then with the polynucleotide [Hunger, H. D., et al, (1981) Biochim. Biophys. Acta 653:344-349].

In general, any method can be employed for immobilizing the probe, provided that the complementary single stranded sequence is available for hybridization to sample nucleic acids. Particular methods or materials are not critical to the present invention.

A particularly attractive alternative to employing directly immobilized probe is to use an immobilizable form of probe which allows hybridization to proceed in solution where the kinetics are more rapid. Normally in such embodiment, one would use a probe which comprises a reactive site capable of forming a stable covalent or noncovalent bond with a reaction partner and obtain immobilization by exposure to an immobilized form of such reaction partner. Preferably, such reactive site in the probe is a binding site such as a biotin or hapten moiety which is capable of specific noncovalent binding with a binding substance such as avidin or an antibody which serves as the reaction partner.

Essentially any pair of substances can comprise the reactive site/reactive partner pair which exhibit an appropriate affinity for interacting to form a stable bond, that is a linking or coupling between the two which remains substantially intact during the subsequent assay steps, principally the separation and detection steps. The bond formed may be a covalent bond or a noncovalent interaction, the latter being preferred especially when characterized by a degree of selectivity or specificity. In the case of such preferred bond formation, the reactive site on the probe will be referred to as a binding site and the reaction partner as a binding substance with which it forms a noncovalent, commonly specific, bond or linkage.

In such preferred embodiment, the binding site can be present in a single stranded hybridizable portion or in a single or double stranded nonhybridizable portion of the probe or can be present as a result of a chemical modification of the probe. Examples of binding sites existing in the nucleotide sequence are where the probe comprises a promoter sequence (e.g., lac-promoter, trp-promoter) which is bindable by a promoter protein (e.g., bacteriophage promoters, RNA polymerase), or comprises an operator sequence (e.g., lac operator) which is bindable by a repressor protein (e.g., lac repressor), or comprises rare, antigenic nucleotides or sequences (e.g., 5-bromo or 5-iododeoxyuridine, Z-DNA) which are bindable by specific antibodies [see also British Pat. Spec. 2,125,964]. Binding sites introduced by chemical modification of the polynucleotide comprised in the probe are particularly useful and normally involve linking one member of a specific binding pair to the probe nucleic acid. Useful binding pairs from which to choose include biotin/avidin (including egg white avidin and streptavidin), haptens and antigens/antibodies, carbohydrates/lectins, enzymes/inhibitors, and the like. Where the binding pair consists of a proteinaceous member and a nonproteinaceous member, it will normally be preferred to link the nonproteinaceous member to the probe since the proteinaceous member may be unstable under the denaturing conditions of hybridization of the probe. Preferable systems involve linking the probe with biotin or a hapten and employing immobilized avidin or anti-hapten antibody reagent, respectively.

When the probe is presented for hybridization with the sequence of interest in an immobilizable form, the subsequent steps of immobilization of the formed duplexes through a property of the probe and addition of the anti-hybrid antibody reagent can proceed in any desired order. Immobilization and anti-hybrid addition can be accomplished by simultaneous addition of the involved reagents and materials, or one can precede the other, with or without intervening wash or separation steps, in either order. Where ordered additions are followed, of course one will take into account the concentrations of the added reagents so as not to oversaturate the formed hybrids and inhibit interaction therewith of the second added materials.

Although immobilized probes or immobilizable probes which become bound to solid supports by specific binding processes described above are preferred, immobilizable probes can be bound to supports by processes with relatively low specificity. In this case the support would bind the hybridized probe but not the unhybridized form. Then the amount of hybrid would be measured with the antibody reagent. An example of a support of this type is hydroxyapatite which binds DNA.RNA and RNA.RNA duplexes but not the single stranded species [Brenner and Falkow, Adv. in Genet., 16:81(1973)].

Also, a chemically active or activatable group can be introduced into the probe and allowed to react with the solid support following the hybridization. This system would give a covalently immobilized probe and the amount of hybrid coupled to the support can be determined with the antibody reagent.

Anti-Hybrid Antibody Reagent and Detection Schemes

The antibody reagent of the invention is principally characterized by its ability to bind the DNA.RNA or RNA.RNA hybrids formed between the probe and complementary sample nucleic acids to the significant exclusion of single stranded polynucleotides. As stated previously above, the antibody reagent can consist of whole antibodies, antibody fragments, polyfunctional antibody aggregates, or in general any substance comprising one or more specific binding sites from an antibody for RNA.RNA or DNA.RNA, as the case may be. When in the form of whole antibody, it can belong to any of the classes and subclasses of known immunoglobulins, e.g., IgG, IgM, and so forth. Any fragment of any such antibody which retains specific binding affinity for the hybridized probe can also be employed, for instance, the fragments of IgG conventionally known as Fab, F(ab'), and F(ab')$_2$. In addition, aggregates, polymers, derivatives and conjugates of immunoglobulins or their fragments can be used where appropriate.

The immunoglobulin source for the antibody reagent can be obtained in any available manner such as conventional antiserum and monoclonal techniques. Antiserum can be obtained by well-established techniques involving immunization of an animal, such as a mouse, rabbit, guinea pig or goat, with an appropriate immunogen. The immunoglobulins can also be obtained by somatic cell hybridization techniques, such resulting in what are commonly referred to as monoclonal antibodies, also involving the use of an appropriate immunogen.

Immunogens for stimulating antibodies specific for DNA.RNA hybrids can comprise homopolymeric or heteropolymeric polynucleotide duplexes. Among the possible homopolymer duplexes, particularly preferred is poly(rA).poly(dT) [Kitagawa and Stollar (1982) Mol. Immunol. 19:413]. However, in general, heteropolymer duplexes will be preferably used and can be prepared in a variety of ways, including transcription of $\phi$X174 virion DNA with RNA polymerase [Nakazato (1980) Biochem. 19:2835]. The selected RNA.DNA duplexes are adsorbed to a methylated protein, or otherwise linked to a conventional immunogenic carrier material, such as bovine serum albumin, and injected into the desired host animal [see also Stollar (1980) Meth. Enzymol. 70:70].

Antibodies to RNA.RNA duplexes can be raised against double stranded RNAs from viruses such as reovirus or Fiji disease virus which infects sugar cane, among others. Also, homopolymer duplexes such as poly(rI).poly(rC) or poly(rA) poly(rU), among others, can be used for immunization as above.

The binding of the antibody reagent to the hybridized probe duplex according to the present method can be detected by any convenient technique. Advantageously, the antibody reagent will itself be labeled with a detectable chemical group. Such detectable chemical group can be any material having a detectable physical or chemical property. Such materials have been well-developed in the field of immunoassays and in general most any label useful in such methods can be applied to the present invention. Particularly useful are enzymatically active groups, such as enzymes (see Clin. Chem. (1976)22:1243, U.S. Pat. No. 31,006 and UK Pat. 2,019,408), enzyme substrates (see U.S. Pat. No. 4,492,751, cofactors (see U.S. Pat. Nos. 4,230,797 and 4,238,565), and enzyme inhibitors (see U.S. Pat. No. 4,134,792); fluorescers (see Clin. Chem. (1979)25:353); chromophores; luminescers such as chemiluminescers and bioluminescers (see U.S. Pat. No. 4,380,580); specifically bindable ligands such as biotin (see European Pat. Spec. 63,879) or a hapten (see PCT Publ. 83-2286); and radioisotopes such as $^3$H, $^{35}$S, $^{32}$P, $^{125}$I, and $^{14}$C. Such labels and labeling pairs are detected on the basis of their own physical properties (e.g., fluorescers, chromophores and radioisotopes) or their reactive or binding properties (e.g., enzymes, substrates, cofactors and inhibitors). For example, a cofactor-labeled antibody can be detected by adding the enzyme for which the label is a cofactor and a substrate for the enzyme. A hapten or ligand (e.g., biotin) labeled antibody can be detected by adding an antibody to the hapten or a protein (e.g., avidin) which binds the ligand, tagged with a detectable molecule. Such detectable molecule can be some molecule with a measurable physical property (e.g., fluorescence or absorbance) or a participant in an enzyme reaction (e.g., see above list). For example, one can use an enzyme which acts upon a substrate to generate a product with a measurable physical property. Examples of the latter include, but are not limited to, $\beta$-galactosidase, alkaline phosphatase and peroxidase. Other labeling schemes will be evident to one of ordinary skill in the art.

Alternatively, the antibody reagent can be detected based on a native property such as its own antigenicity. A labeled anti-(antibody) antibody will bind to the primary antibody reagent where the label for the second antibody is a conventional label as above. Further, antibody can be detected by complement fixation or the use of labeled protein A, as well as other techniques known in the art for detecting antibodies.

Where the antibody reagent is labeled, as is preferred, the labeling moiety and the antibody reagent are associated or linked to one another by direct chemical linkage such as involving covalent bonds, or by indirect linkage such as by incorporation of the label in a microcapsule or liposome which is in turn linked to the antibody. Labeling techniques are well-known in the art and any convenient method can be used in the present invention.

Reaction Mixture

The test sample to be assayed can be any medium of interest, and will usually be a liquid sample of medical veterinary, environmental, nutritional, or industrial significance. Human and animal specimens and body fluids particularly can be assayed by the present method, including urine, blood (serum or plasma), milk, cerebrospinal fluid, sputum, fecal matter, lung aspirates, throat swabs, genital swabs and exudates, rectal swabs, and nasopharnygal aspirates. Where the test sample obtained from the patient or other source to be tested contains principally double stranded nucleic acids, such as contained in cells, the sample will be treated to denature the nucleic acids, and if necessary first to release nucleic acids from cells. Denaturation of nucleic acids is preferably accomplished by heating in boiling water or alkali treatment (e.g., 0.1 N sodium hydroxide), which if desired, can simultaneously be used to lyse cells. Also, release of nucleic acids can, for example, be obtained by mechanical disruption (freeze/thaw, abrasion, sonication), physical/chemical disruption (detergents such as polyoxyethylene ether detergents available from Rohm & Haas, Phila., Pa. USA, under the Triton ® trademark, polyoxytheylenesorbitan detergents known as Tween and available from Sigma Chemical Co., St. Louis, Mo. USA, sodium dodecylsulfate, alkali treatment, osmotic shock, or heat), or enzymatic lysis (lysozyme, proteinase K, pepsin). The resulting test medium will contain nucleic acids in single stranded form which can then be assayed according to the present hybridization method.

As is known in the art, various hybridization conditions can be employed in the assay. Typically, hybridization will proceed at slightly elevated temperatures, e.g., between about 35 and 75° C. and usually around 65° C., in a solution comprising buffer at pH between about 6 and 8 and with appropriate ionic strength (e.g., 2XSSC where 1XSSC=0.15M sodium chloride and 0.015M sodium citrate, pH 7.0), protein such as bovine serum albumin, Ficoll (a trademark identifying a copolymer of sucrose and epichlorohydrin sold by Pharmacia Fine Chemicals, Piscataway, N.Y.), polyvinylpyrrolidone, and a denatured foreign DNA such as from calf thymus or salmon sperm). The degree of complementarity between the sample and probe strands required for hybridization to occur depends on the stringency of the conditions. The extent and specificity of hybridization is affected by the following principal conditions:

1. The purity of the nucleic acid preparation.
2. Base composition of the probe—G-C base pairs will exhibit greater thermal stability than A-T or A-U base pairs. Thus, hybridizations involving higher G-C content will be stable at higher temperatures.
3. Length of homologous base sequence—Any short sequence of bases (e.g., less than 6 bases), has a high degree of probability of being present in many nucleic acids. Thus, little or no specificity can be attained in hybridizations involving such short sequences. The present homologous probe sequence will be at least 10 bases, usually 20 bases or more, and preferably greater than 100 bases. From a practical standpoint, the homologous probe sequence will often be between 300-1000 nucleotides.
4. Ionic strength—The rate of reannealing increases as the ionic strength of the incubation solution increases. Thermal stability of hybrids also increases.
5. Incubation temperature—Optimal reannealing occurs at a temperature about 25°-30° C. below the melting temperature (Tm) for a given duplex. Incubation at temperatures significantly below the optimum allows less related base sequences to hybridize.
6. Nucleic acid concentration and incubation time—Normally, to drive the reaction towards hybridization, one of the hybridizable sample nucleic acid or probe nucleic acid will be present in excess, usually 100 fold excess or greater.
7. Denaturing reagents—The presence of hydrogen bond disrupting agents such as formamide and urea increases the stringency of hybridization.
8. Incubation—The longer the incubation time, the more complete will be the hybridization.
9. Volume exclusion agents—The presence of these agents, as exemplified by dextran and dextran sulfate, are thought to increase the effective concentrations of the hybridizing elements thereby increasing the rate of resulting hybridization.

Normally, the temperature conditions selected for hybridization will be incompatible with the binding of antibody reagent to formed hybrids and detection of the label response. Accordingly, the antibody reagent binding step and label detection step will proceed after completion of the hybridization step. The reaction mixture will usually be brought to a temperature in the range of from about 3° C. to about 40° C. and the binding and detection steps then performed. Dilution of the hybridization mixture prior to addition of antibody reagent is desirable when the salt and/or formamide concentrations are high enough to interfere significantly with the antibody binding reaction.

It might be found in a particular assay situation using an RNA probe that the probe is subject to partial degradation by alkaline hydrolysis of the phosphodiester bonds or by the presence of ribonucleases. In the former case, hydrolysis can be controlled by avoiding exposure of the probe to a pH higher than about 10. Ribonucleases can be effectively inhibited by the presence of such substances as sodium dodecylsulfate, aurintricarboxylic acid, ribonucleoside vanadyl complexes, heparin, diethylpyrocarbonate, and proteinaceous inhibitors isolated from mammalian sources.

Reagent System

The present invention additionally provides a reagent system, i.e., reagent combination or means, comprising all of the essential elements required to conduct a desired assay method. The reagent system is presented in a commercially packaged form, as a composition or admixture where the compatability of the reagents will allow, in a test device configuration, or more usually as a test kit, i.e., a packaged combination of one or more containers, devices, or the like holding the necessary reagents, and usually including written instructions for the performance of assays. Reagent systems of the present invention include all configurations and compositions for performing the various hybridization formats described herein.

In all cases, the reagent system will comprise (1) an immobilized or immobilizable probe as described herein, and (2) the antibody reagent, preferably labeled with a detectable chemical group. A test kit form of the system can additionally include ancillary chemicals such as the components of the hybridization solution and denaturation agents capable of converting double stranded nucleic acids in a test sample into single stranded form. Preferably, there is included a chemical lysing and denaturing agent, e.g., alkali, for treating the sample to release single stranded nucleic acid therefrom.

The present invention will now be illustrated, but is not intended to be limited, by the following examples.

EXAMPLE 1

Hybridization Assay For Detecting Bacteriuria Using An Immobilized RNA Probe

A. Preparation of the RNA Probe

An 800 base pair fragment of the tuf A gene which encodes for the protein EF-Tu in *Escherichia coli* is derived from the bacteriophage M13-10 (ATCC 39403-131). The fragment is cloned between Hind III and Eco RI restriction endonuclease sites of M13mp9 (New England Biolabs, Beverly, Mass.). This plasmid is grown in an E. coli host JM103 (Δlac, pro), supE, thi, strA, sbcB15, hsdR4, F'traD36, proABlac IqZM15. The tuf A fragment is excised from M13-10 and cloned into the Hind III and Eco RI sites of the pSP64 plasmid vector available from Promega Biotec., Madison, Wis.

A 15 mL overnight culture of *E. coli* JM103 carrying the pSP64 plasmid containing the tuf A fragment is inoculated into one liter of 2xYT broth in a two liter flask. The culture is incubated at 37° C. for 3 hours and the cells are harvested. They are lysed and the DNA is isolated by phenol/chloroform extractions. The closed circular plasmid DNA is purified by centrifugation in a cesium chloride-ethidium bromide gradient [Maniatis, T., Fritsch, E. F. and Sambrook, J., Molecular Cloning, Cold Spring Harbor Laboratory, Cold Spring Harbor, N.Y. (1982)].

The purified plasmid is chromatographed on Sephadex G-50 (Pharmacia Fine Chemicals, Piscataway, N.J.) in 10 mM Tris-hydrochloride buffer, pH 7.5, containing 0.1 M NaCl and 1 mM EDTA. The effluent containing DNA is collected and the DNA is precipitated with cold ethanol. The precipitate is taken up in 10 mM NaCl, 10 mM $MgCl_2$ and 1 mM dithiothreitol and digested for 1 hour with 1 unit EcoRI per microgram ($\mu$g) DNA. Then, the reaction mixture is extracted once with phenol/chloroform and once with chloroform, and the DNA is precipitated with cold ethanol. The precipitate is dissolved in 10 mM Tris-hydrochloride buffer, pH 7.4, to give 500 $\mu$g DNA/mL.

A 500 microliter ($\mu$L) reaction mixture is prepared with the following composition: 50 $\mu$g of the EcoRI digest; 40 mM Tris-hydrochloride buffer, pH 7.5; 6 mM $MgCl_2$; 2 mM spermine; 0.5 mM ATP, CTP, UTP and GTP; 10 mM dithiothreitol; 500 units RNasin (Promga Biotec) and 50 units of RNA polymerase from bacteriophage SP6 (Promega Biotec). The reaction is allowed to stand for 1 hour at room temperature and then 50 units of additional RNA polymerase is added and allowed to react for another hour.

DNA in the reaction is digested for 10 minutes at 37° C. with 10 $\mu$g of RNase-free DNase. The reaction mixture is extracted with phenol/chloroform and chromatographed on Sephadex G-50 in 10 mM Tris-hydrochloride buffer, pH 7.4, 0.1 M NaCl. The RNA is collected and precipitated with cold ethanol. The precipitate is dissolved in 50 mM sodium acetate buffer, pH 5.0, containing 1 mM EDTA.

The RNA probe described above is immobilized on acrylic beads with reactive epoxide groups available under the tradename Eupergit C from Accurate Chemical and Scientific Corp., Westbury, N.Y. Three milliliters (3 mL) of 50 mM sodium acetate buffer, pH 4.5, containing 250 $\mu$g of RNA probe is shaken at room temperature for 10 hours with 200 mg of Eupergit C. The buffer is removed and assayed for RNA to determine the extent of immobilization that has occurred.

The resin is then washed by shaking briefly with 1 mL of 0.1 M sodium phosphate buffer, pH 6.5, containing 1.2 M NaCl, 0.5% (w/v) sodium dodecylsulfate, 1 mg polyvinylpyrrolidone/mL, and 5 mg bovine serum albumin/mL. This hybridization solution is removed and replaced by 1 mL of fresh hybridization solution and the suspension incubated at 65° C. for 1 hour to remove noncovalently bound RNA probe. The solution is removed and the resin-RNA probe conjugate is suspended in 50 mL of the hybridization solution.

B. Preparation of methylated thyroblobulin

One hundred milligrams of bovine thyroglobulin (Sigma Chemical Co., St. Louis Mo.) is combined with 10 ml of anhydrous methanol and 400 $\mu$l of 2.55 M HCl in methanol. This mixture is stirred on a rotary mixer at room temperature for 5 days. The precipitate is collected by centrifugation and washed twice with methanol and twice with ethanol. Then it is dried under vacuum overnight. About 82 mg of dry powder is obtained.

C. Preparation of Antibody to DNA.RNA Hybrid

A DNA.RNA hybrid is prepared by transcription of $\phi$X174 virion DNA with RNA polymerase as described by Nakazato [Biochem. 19:2835(1980)]. One hundred fifty (150) micrograms ($\mu$g) of the hybrid in 250 $\mu$L of 20 mM Tris-hydrochloride buffer, pH 7.4, 1 mM EDTA is combined with 150 $\mu$g of methylated thyroglobulin in 250 $\mu$L water. A precipitate forms and is suspended in Tris-buffer. This mixture is emulsified with an equal volume of Freunds adjuvant. Mice are each immunized with 0.5 ml of the suspension and when serum antibody titers to RNA.DNA develop, hybridomas are prepared and screened for monoclonal antibody specific for RNA.DNA [Stuart et al (1981) Proc. Natl. Acad. Sci. USA 78, 3751, Galfre and Milstein (1981) Meth. in Enzymol. 73, 1].

The cloned hybridomas are propagated in the peritoneal cavity of mice to generate a large quantity of antibody. The ascites fluid is applied to a column of Affigel-Blue resin (Bio-Rad Laboratories, Richmond, VA) equilibrated with 10 mM Tris-hydrochloride buffer, pH 8.0, 0.15 M NaCl. This chromatography removes albumin and the eluted protein which contains the antibody is chromatographed on DEAE-Sepharose (Pharmacia Fine Chemicals). The chromatography is developed with a linear gradient of 10 mM Tris-hydrochloride, pH 8.0, to 10 mM Tris-hydrochloride, pH 8.0, 200 mM NaCl. The major peak of eluted protein contains the monoclonal antibody free of transferrin and albumin.

D. Preparation of $\beta$-Galactosidase-Antibody Conjugate

Sulfhydryl residues on $\beta$-galactosidase are exposed by reduction with dithiothreitol. $\beta$-galactosidase (30,000 units, grade VIII, Sigma Chemical Co., St. Louis, Mo.) in 2 mL of 0.1 M N-2-hydroxyethyl-piperazine-N'2-ethane sulfonate (HEPES), pH 7.0, 0.09 M NaCl, is combined with 3.5 $\mu$mol of dithiothreitol and allowed to stand at room temperature for 4 hours. The dithiothreitol is removed by chromatography on a 2.5×80 cm column of Sepharose 6B Cl (Pharmacie Fine Chemicals) in the buffer described above. Fractions containing protein are combined into a pool. The number of moles of sulfhydryl groups per mole of enzyme is measured by the method of Ellman [Ellman (1959) Arch. Biochem. Biophys. 82, 70].

Succinimidyl-4-(N-maleimidomethyl) cyclohexane-1-carboxylate (SMCC) (Pierce Chemical Co., Rockford, Ill., 5.3 mg, is dissolved in 250 $\mu$L of anhydrous N,N-dimethylformamide and a 40 $\mu$L aliquot is added to 3 mL of 0.1 M HEPES buffer, pH 7.0, 0.15 M NaCl. A 25 $\mu$L aliquot of this aqueous solution is added to 825 $\mu$L of HFPES/NaCl buffer and 100 $\mu$L of 1 mM glutathione. When this reaction mixture has stood at room temperature for 15 minutes, the unreacted glutathione is determined by Ellman's method.

Monoclonal antibody to DNA.RNA is combined with 400 $\mu$mol of SMCC in a final volume of 533 $\mu$L of HEPES/0.15 M NaCl buffer and allowed to react for 1 hour at 30° C. The reaction mixture is chromatographed on a 1×24 cm column of Biogel P-2 resin (Bio-Rad Laboratories, Richmond, Calif.) and eluted with HEPES/0.15 M NaCl buffer. Effluent containing protein is pooled, and the protein concentration is determined by the method of Sedmack and Grossberg Anal. Biochem. 79, 544(1977)]and the number of maleimide groups determined by titration with glutathione as described above.

A 2.8 mg portion of the antibody-maleimide adduct is combined with 10 mg of dithiothreitol treated $\beta$-galactosidase and allowed to react for 4 hours at room temperature. The reaction mixture is chromatographed at 4° C. on a 2.5×80 cm column of Sepharose 6B Cl in HEPES/0.15 M NaCl at 4° C. The flow rate is set at 4 mL/hour and 3 mL fractions are collected. Fractions are assayed for $\beta$-galactosidase activity and antibody binding activity. Fractions having both activities are pooled.

E. Hybridization Assay

Ten milliliter aliquots of urine from patients with possible urinary tract infections are centrifuged at 10,000×g for ten minutes and the supernatants decanted and discarded. The sediments are suspended in 50 $\mu$L of 10 mM Tris-hydrochloride buffer, pH 8.0, containing 20 mg of egg white lysozyme/mL (Sigma Chemical Co., St. Louis, Mo). 0.1 M NaCl, and 5 mM EDTA. The reaction is allowed to stand at room temperature for 30 minutes and then 10 $\mu$L of 1 M NaOH is added and this alkaline mixture is allowed to stand at room temperature for 10 minutes to denature DNA from any bacteria in the original specimen. The reaction mixtures are neutralized by addition of 250 $\mu$L of the buffered suspension of the resin-RNA conjugate described previously. This hybridization system is incubated at about 65° C. for 15 hours with gentle agitation.

The resin-RNA probe conjugate is allowed to settle and the liquid is decanted. The resin is washed twice by suspension in 0.5 mL each time of 0.1 M sodium phosphate buffer, pH 7.4, 5 mg bovine serum albumin/mL. The resin is combined with 300 $\mu$l of 0.1 M sodium phosphate buffer, pH 7.4, containing 10 mM $MgCl_2$, 5 mg bovine serum albumin/mL, and 0.4 $\mu$g $\mu$-galactosidase-antibody/mL (anti-DNA.RNA). The mixture is agitated gently for hour at room temperature and the resin washed twice, one minute each, with 5 mL of 0.1 M sodium phosphate buffer, pH 7.4, containing 0.1% Tween 20 (polyoxyethylenesorbitan monolaurate, Sigma Chemical Co.) detergent. The washed resin is agitated gently for 30 minutes at room temperature in 1.0 mL of 0.1 M sodium phosphate buffer, pH 7.4, containing 800 $\mu$M 7-$\beta$-galactosyl-3-[6-aminohexylcarboxamide]coumarin [Worah et al (1981) Clin. Chem. 27:673]. At the end of this incubation, the fluorescence of the solution is recorded using 400 nanometers (nm) excitation and 450 nm emission.

Fluorescence signals developed with urine specimens containing greater than 100,000 bacteria per ml will be significantly higher than those containing less than 5000 bacteria per mL. This method can be used as a qualitative test for bacteriuria.

EXAMPLE 2

Hybridization Assay For *E. Coli* 23s Ribosomal RNA Using An Immobilized DNA Probe A. DNA probe for 23s RNA The DNA probe is an EcoRI/BglII fragment from the rrnD operon which codes for 23s RNA in E. coli Jinks-Robertson et al (1983) Cell. 33:865]. The probe encompasses about two-thirds of the 23s RNA sequence from the 3'-hydroxyl and is cloned into an M13 virus vector to give single stranded virion DNA which is complementary to cellular ribosomal RNA. The M13 virus is grown in *E. coli* strain JM103 and is isolated from culture medium by precipitation with polyethylene glycol. The virion DNA is purified from the virus particles by phenol extraction [Maniatis, et al, supra].

The purified DNA is made 0.3 M in NaOH and incubated at 37° C. for 4 hours to degrade contaminating RNA. The mixture is neutralized by addition of 30% acetic acid and the DNA is precipitated with cold ethanol.

B. Antibody to DNA.RNA

Mice are immunized with DNA.RNA hybrid as described in Example 1 and spleen cells are fused with SP 2/0-Ag14 myeloma cells (available from American Type Culture Collection, Rockville, Md.). Hybridomas secreting antibodies specific for DNA.RNA are identified as outlined above. The most preferred hybridoma is that deposited with the American Type Culture Collection, Rockville, Md. as ATCC HB 8730.

Antibodies are purified from ascites fluid by HPLC using a LDC/Milton Roy liquid chromatograph equipped with CI~10 integrator. The ascites fluid is dialyzed against 0.01 M potassium phosphate buffer, pH 6.8, centrifuged to remove particulate matter, and passed through a 0.22 μm nitrocellulose filter. One to two milliliters of processed ascites fluid is applied to a 10×250 mm anion-exchange column equilibrated with 0.01 M potassium phosphate, pH 6.84. The chromatography is developed with a 60 min linear gradient from 0.01 M potassium phosphate buffer, pH 6.84, to 0.085 M potassium phosphate, pH 6.40, at a flow rate of 1 mL/min. The peak containing IgG is concentrated, dialyzed against phosphate buffered saline, pH 7.4, centrifuged to remove any denatured protein, and the IgG concentration is determined on the basis of absorbance at 280 nm using $E_{1\,cm}^{1\,mg/mL} = 1.40$.

C. Immobilization of the DNA probe

Meta-nitrophenyl groups are introduced onto cellulose powder and subsequently converted to the diazonium salt for covalent immobilization of the DNA.

1-[(m-Nitrobenzyloxy)methyl]pyridinium chloride (690 mg, 2.46 mmole) (Aldrich Chemical Co., Milwaukee, Wis.) is combined with 128 mg sodium acetate in 7.7 mL water. Two grams of Sigmacell, type 20 cellulose (Sigma Chemical Co.) is added and mixed for about 15 minutes in a beaker immersed in a water bath at 60° C. The cellulose becomes nearly dry and it is placed in an oven at 135°-140° C. for 45 minutes. Good incorporation of m-nitrophenyl residues is dependent on maintaining the temperature as high as possible during this period. If the temperature is too high the cellulose carmelizes.

Following the baking step, the cellulose is suspended in water and lumps are broken up by rubbing the cellulose in water until the particles pass through a 150 μm wire sieve. The cellulose is washed three times with 120 mL each, of water and twice with 50 ml, each, of ethanol. Then it is dried overnight in vacuo.

Nitrophenyl groups on the cellulose are reduced by incubating it at 65° C. for 1 hour in 10 ml of 0.1 M $Na_2CO_3$ containing 2.0 g sodium dithionite. Then the cellulose is washed several times with water on a scintered glass funnel and once with 30% acetic acid. Finally it is washed three more times with water and dried in vacuo at 40° to 50° C. overnight.

Two hundred and fifty milligrams of the reduced cellulose is added to 5.0 mL of 1.2 M HCl at 0° C. and 13 μL of 100 mg $NaNO_2$/mL is added. This mixture is allowed to stand for 1.0 hour and during this period the mixture is tested for the presence of $NaNO_2$ with starch-iodide paper. If the test is weak or negative, 20 μL of the $NaNO_2$ is added.

At the end of the reaction period the cellulose is washed successively with 30 to 50 mL of cold (0° C.) water on a cold sintered glass funnel, with 10 to 15 ml of cold 10 mM urea, with more cold water and finally with about 10 mL of cold 0.2 M sodium acetate buffer, pH 4.0. The cellulose is transferred quickly to a flask containing 0.92 mL of cold 0.2 M sodium acetate buffer, pH 4.0, containing 69 μg of the DNA probe.

The mixture is shaken at 0° to 4° C. for 15 hours and then washed with 1×SSPE (20 mM sodium phosphate buffer, pH 7.8, 0.18 M NaCl, 1 mM EDTA), 0.1% sodium dodecylsulfate (SDS) on a scintered glass funnel. The cellulose is incubated at 55° C. for 4 hours in a hybridization solution composed of:

| | |
|---|---|
| 2.0 mL | formamide |
| 1.5 mL | 20 × SSPE |
| 0.3 mL | 10 mg bovine serum albumin/mL, 10 mg Ficoll/mL, 10 mg polyvinyl pyrrolidone/mL |
| 0.03 mL | 10% SDS (w/v) |
| 0.140 ml | 4.25 mg salmon sperm DNA/mL |

Prior to use, the salmon sperm DNA is incubated at 37° C. for 17 hours in 0.3 M NaOH, neutralized with 30% acetic acid and collected by precipitation with cold (−15° C.) ethanol.

Following the incubation at 55° C., the cellulose is washed twice with about 10 mL each of 1×SSPE, 0.1% SDS. The cellulose is resuspended in 5.0 mL of the hybridization solution and 0.2 mL aliquots of the slurry are dispensed into reaction tubes for hybridization.

D. Preparation of 23s ribosomal RNA

Ribosomal RNA is prepared from E. coli and the 23s component is isolated by sucrose density gradient centrifugation [Takanami, M., (1967) Meth. Enzymol., 12A:491; McConkey, E. H. (1967) Meth. Enzymol., 12A:620].

E. Hybridization assay for 23s RNA

The hybridization solution is aspirated from the reaction tubes containing the cellulose with the immobilized DNA probe. Then 100 μL of hybridization solution containing 10 ng 23s RNA/mL is added to each tube and they are incubated at 55° C. for indicated periods. At the ends of the incubations the hybridization solutions are removed and the cellulose is washed with 0.5 ml 1 x SSPE, 0.1% SDS, incubated at 55° C. for 30 minutes in 0.5 mL of 1 ×SSPE, 0.1% SDS and washed once with 0.5 ml of 1 ×SSPE, 0.1% SDS.

The amounts of DNA.RNA formed are measured by immunoassay. The cellulose in each tube is shaken at room temperature for 30 minutes with 50 μL of 20 mM sodium phosphate buffer, pH 7.4, containing 0.15 M NaCl, 1 mM EDTA, 0.5% (v/v) Tween 20 (polyoxyethylenesorbitan monolaurate, Sigma Chemical Co.) and 5.0 mg BSA/mL. Then 100 μL of this solution containing 1.0 μg antibody to DNA.RNA is added to each tube and the shaking is continued for 30 minutes. The liquid is removed by aspiration and the cellulose is washed four times with 0.5 mL each of 0.1 M Tris.nydrochloride buffer, pH 8.0, containing 5 mM $MgCl_2$, 0.5% Tween-20 and 5.0 mg bovine albumin/mL (Tris/$MgCl_2$/Tween/BSA). Then 150 μL of alkaline phosphatase labeled antimouse IgG (Sigma Chemical Co.) diluted 200-fold in Tris/$MgCl_2$/Tween/BSA is added to each tube and shaken at room temperature for 1.0 hour.

The cellulose from each assay is washed twice with 0.5 mL each of Tris/$MgCl_2$/Tween/BSA containing 0.5 M NaCl and then the cellulose is transferred to clean test tubes using 1.5 to 2.0 mL of this buffer solution. The buffer is removed and the alkaline phosphatase label bound to the cellulose is measured.

For this purpose, 200 μL of 1.0 M diethanolamine-hydrochloride buffer, pH 9.8 containing 1 mM $MgCl_2$ and 1 mg p-nitrophenylphosphate/mL is added and incubated at 25° C. for 30 minutes. Then the enzyme catalyzed reaction is quenched by addition of 1.5 mL 0.1 M $Na_3PO_4$ and the absorbances at 405 nm are recorded. The results are as follows:

| Hybridization Time (Hrs) | Absorbance |
| --- | --- |
| 0 | 0.34 |
| 0.5 | 1.18 |
| 1.0 | 1.36 |
| 2.0 | 1.85 |
| 8.0 | 2.27 |
| 12.0 | 2.32 |
| 24.0 | 2.34 |

The absorbances increase with hybridization time indicating increasing amounts of DNA.RNA hybrids had formed.

EXAMPLE 3

Hybridization Assay for 23s Ribosomal RNA Using an Immobilizable DNA Probe

The sample RNA is hybridized with a soluble DNA probe with appended biotin residues. Then the hybridized and unhybridized DNA probe are bound to a solid support with immobilized streptavidin. The amount of DNA.RNA on the support is measured by an immunoassay using enzyme-labeled antibody to DNA.RNA.

A. Biotinylated Probe DNA

The M-13 virus described above in Example 2 with the insert complementary to 23s RNA is propagated in E. coli strain JM103 and the bacterial cells are harvested for isolation of the replicative form of the viral DNA. This double stranded DNA is purified by cesium chloride-ethidium bromide density gradient centrifugation [Maniatis, et a., supra].

Biotin residues are introduced into this double stranded DNA by nick translation using biotinylated dUTP available from Enzo Biochem. Inc., NY [Langer, P. R. et al (1981) Proc. Natl. Acad. Sci., 78:6633; Leary, J. J. et al (1983) Proc. Natl. Acad. Sci., 80:4045].

Contaminating RNA is deqraded by treatment with alkali as described in Example 2. Immediately before use the biotinylated probe is denatured by placing the solution in a boiling water bath for four minutes.

B. Immobilization of streptavidin

Streptavidin (Calbiochem-Behring Corp., La Jolla, Calif.) is immobilized on Act-Ultrogel ® AcA 22 (available from LKB Instruments, Inc., Gaithersburg, Md.) which is an acrylamide-agarose support activated with glutaraldehyde [Doley, S. G. et al (1976) FEBS Letters, 65:87]. The immobilization is carried out according to the manufacturer's instructions to give approximately 0.5 $\mu$g streptavidin per 10 $\mu$L of packed Act-Ultrogel AcA 22.

C. Hybridization assay

Two milliliter aliquots of urines suspected of containing bacterial infection are centrifuged at 3000×g to sediment the bacteria and the supernatants are decanted. Ninety microliters of hybridization solution described in Example 2 is added to each pellet and 5 $\mu$L of the biotinylated probe (at a concentration of 0.5 $\mu$g/mL in 20 mM sodium phosphate buffer, pH 7.0, 0.5 mM EDTA) is added. The mixtures are agitated to suspend the pellets (if present) and they are incubated at 55° C. for 4.0 hours.

Then 700 $\mu$L of 20 mM sodium phosphate buffer, pH 7.4, containing 5.0 mg bovine albumin and 50 $\mu$L of the Ultrogel with immobilized streptavidin is added to each mixture to dilute the hybridization solution and immobilize the biotinylated probe. The mixtures are shaken at room temperature for two hours and the liquid is removed from the support.

The amount of DNA.RNA hybrid associated with the Ultrogel support is measured by immunoassay as described in Example 2 for the cellulose support.

For comparison, the unprocessed urines are tested for bacteria by the one microliter loop culture method using MacConkey and blood agar plates. Plates are incubated at 37° C. for 36 hours and colonies are counted.

Urines with high levels of bacteria by the culture method give high absorbances by the hybridization assay.

The present invention has been particularly described and exemplified above. Obviously, many other variations and modifications of the invention may be made without departing from the spirit and scope hereof.

What is claimed is:

1. A nucleic acid hybridization method for determining a polynucleotide having a particular base sequence in a test medium containing single stranded nucleic acids, comprising the steps of:
    (a) combining the test medium with an immobilized polynucleotide probe under hybridization conditions, said immobilized probe comprising at least one single stranded base sequence which is substantially complementary to the sequence in the polynucleotide to be determined and which is (i) substantially composed of RNA when the polynucleotide to be determined is RNA or DNA, or (ii) is substantially composed of DNA or RNA when the polynucleotide to be determined is RNA,
    whereby hybridization of the polynucleotide to be determined with said probe results in the formation of hybrid duplexes that are either DNA.RNA or RAN.RNA, and
    (b) detecting immobilized hybridized probe resulting from step (a) by adding an antibody reagent that binds to either of said DNA.RNA or RNA.RNA duplexes but not both duplex types when formed between the polynculeotide to be determined and the complementary probe and determining the antibody reagent that becomes bound to such duplexes.

2. The method of claim 1 wherein before step(b) the resulting immobilized hybridized nucleic acids from the test medium are separated from the remainder of the reaction mixture.

3. The method of claim 1 wherein the antibody reagent is labeled with a detectable chemical group.

4. The method of claim 3 wherein the detectable chemical group is an enzymatically active group, a fluorescer, a chromophore, a luminescer, a specifically bindable ligand, or a radioisotope.

5. The method of claim 3 wherein the detectable chemical group is an enzyme.

6. The method of claim 3 wherein the labeled antibody reagent which becomes bound to said duplexes is separated from that which does not become so bound and wherein the detectable chemical group is measured in one of the separated fractions.

7. The method of claim 1 wherein the probe is immobilized by being fixed to a solid support.

8. The method of claim 1 wherein the particular polynucleotide to be determined is RNA or DNA and said probe is substantially composed of RNA.

9. The method of claim 1 wherein the particular polynucleotide to be determined is RNA and said probe is substantially composed of DNA.

* * * * *